United States Patent [19]
Feier et al.

[11] Patent Number: 4,726,932
[45] Date of Patent: Feb. 23, 1988

[54] DOSING AND MIXING APPARATUS FOR FLUID MEDIA

[75] Inventors: Markus Feier, Otelfingen; André Rüegg, Zurich; Donald P. Stait, Steinmaur, all of Switzerland

[73] Assignee: Contraves AG, Zurich, Switzerland

[21] Appl. No.: 652,850

[22] Filed: Sep. 21, 1984

[30] Foreign Application Priority Data

Oct. 6, 1983 [CH] Switzerland ............. 448/83

[51] Int. Cl.[4] ............................................. G01N 1/10
[52] U.S. Cl. ................. 422/103; 73/863.72; 73/863.73; 436/180; 422/100
[58] Field of Search ......... 73/863.72, 863.73, 864.81, 73/864.83; 222/370, 148; 422/103, 102; 436/180

[56] References Cited

U.S. PATENT DOCUMENTS

| | | |
|---|---|---|
| 3,192,969 | 7/1965 | Baruch et al. |
| 3,223,123 | 12/1965 | Young .......................... 73/863.72 X |
| 3,549,994 | 12/1970 | Rothermel et al. ............. 436/70 X |
| 3,664,194 | 5/1972 | Barstow . |
| 3,762,609 | 10/1973 | Hagen et al. |
| 3,800,602 | 4/1974 | Jones ............................. 73/863.72 X |
| 3,885,439 | 5/1975 | Stone ................................. 73/863.73 |
| 3,948,104 | 4/1976 | Stephens ...................... 73/864.83 X |
| 3,991,055 | 10/1976 | Godin et al. |
| 4,152,391 | 5/1979 | Cabrera . |
| 4,338,280 | 7/1982 | Ambers et al. |
| 4,391,777 | 7/1983 | Hutson ......................... 436/132 X |
| 4,506,558 | 3/1985 | Bakalyar ........................ 73/863.72 |

FOREIGN PATENT DOCUMENTS 0089937 9/1983 European Pat. Off. .
2130287 6/1975 Fed. Rep. of Germany .

OTHER PUBLICATIONS

Alperstein et al.; A Gas Sampling and Injection Valve for Vacuum Service; Anal. Chem., vol. 38, No. 2, 1966, pp. 366-367.

Primary Examiner—Barry S. Richman
Assistant Examiner—Michael S. Gzybowski

[57] ABSTRACT

A dosing and mixing apparatus for fluid media comprising at least one delivery element and one isolating element. These elements are provided with through-flow or transfer passages and dosing chambers suitably mutually arranged for accomodating and isolating a voluminized specimen quantity or measured dose of test specimen as well as for delivering this measured out dose of test specimen to and mixing this dose of test specimen with a measured dose of thinning agent. The dosing and mixing apparatus manifests itself in that at least one channel suitably associated with the dosing chamber is provided in a surface of one of the elements, such as the isolating element at the surface thereof which faces the delivery element. Each such channel communicates with through-flow openings or circulation passages and is traversed by a cleansing fluid wetting the mutually facing and touching surfaces of the individual delivery and isolating elements in the transport path of the dose of test specimen.

12 Claims, 13 Drawing Figures

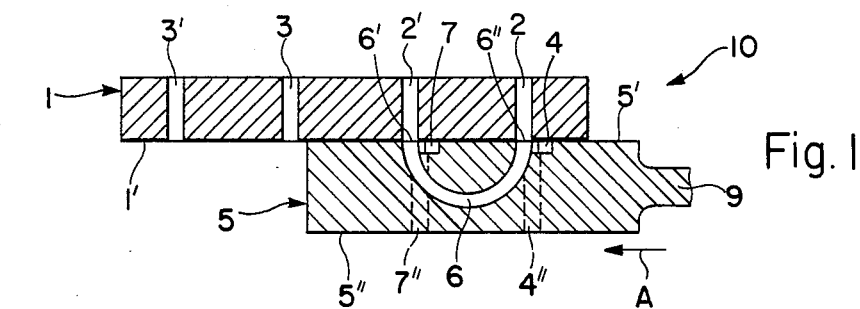
Fig. 1
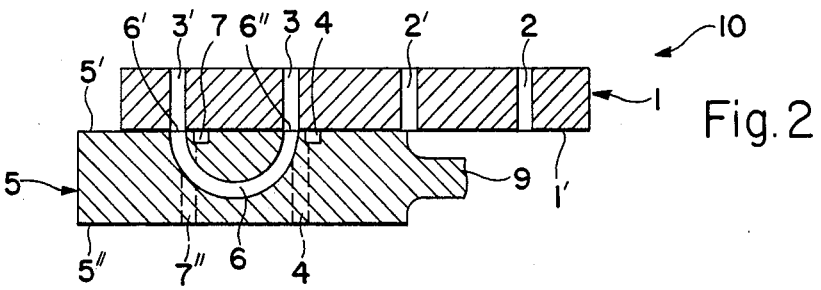
Fig. 2
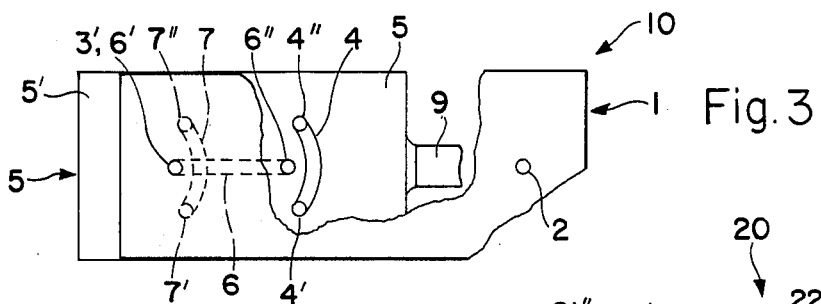
Fig. 3
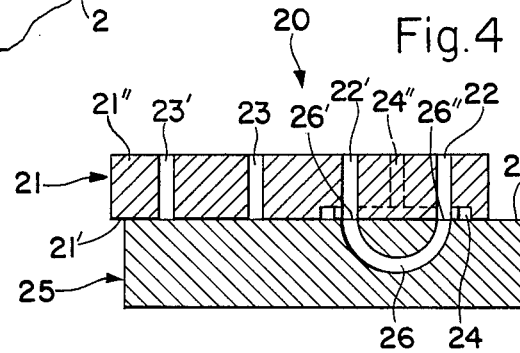
Fig. 4
Fig. 5
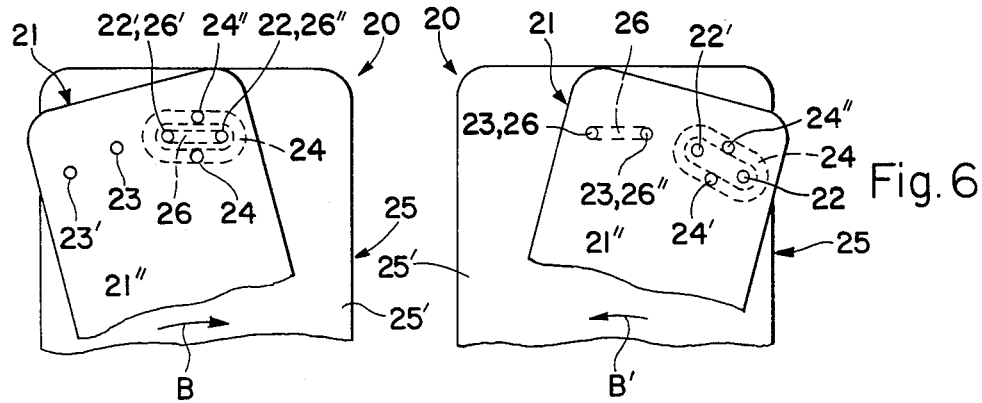
Fig. 6

DOSING AND MIXING APPARATUS FOR FLUID MEDIA

BACKGROUND OF THE INVENTION

The present invention broadly relates to dosing and mixing apparatus and, more specifically, pertains to a new and improved construction of a dosing and mixing apparatus for fluid media Generally speaking, the dosing and mixing apparatus of the present invention comprises at least one delivery element and at least one isolating element. These elements respectively comprise through-flow openings or transfer passages and dosing openings or dosing chambers suitably constructed and suitably mutually arranged for accommodating and isolating at least one voluminized specimen quantity or at least one measured dose of test specimen as well as for delivering this dose of test specimen to and mixing this dose of test specimen with a voluminized thinning agent i.e. a measured dose of diluent or thinning agent.

A dosing and distributing apparatus is known from the German Patent publication No. 1,773,226, which essentially comprises two outer components and an intermediate component arranged therebetween and journaled to pivot about a shaft. Transfer openings or passages are provided in the individual plate-like components in suitable mutual arrangement and can be either brought into communication with one another or interrupted by a suitable pivoting motion of the intermediate component. This apparatus serves for accommodating and isolating a predetermined specimen quantity and for mixing this specimen quantity with a predetermined quantity of thinning agent.

A further dosing and distributing apparatus is known from the German Pat. No. 2,854,303, which is composed essentially of a rotatable intermediate component as well as a first and second stationary external component. The intermediate component and both external components are constructed as discs and are arranged coaxially upon a spindle. The external components are in contact with the intermediate component by means of surfaces facing toward the intermediate component. These individual components are provided with suitably constructed and arranged transfer apertures for accommodating, isolating and delivering a fluid specimen quantity with a quantity of thinning agent.

In the known dosing and distributing apparatuses, the fluid specimen to be analyzed, for instance a blood specimen, is transported from a first position into a second position for charging it with a predetermined quantity of thinning agent. Viscous-film specimen deposits arise in this procedure, especially in the transfer region between the surfaces of the individual components or elements in mutual contact, which cause an adhesive effect which interferes with operation and therefore requires costly maintenance and cleansing work at relatively short time intervals.

SUMMARY OF THE INVENTION

Therefore, with the foregoing in mind, it is a primary object of the present invention to provide a new and improved construction of a dosing and mixing apparatus for fluid media which does not exhibit the aforementioned drawbacks and shortcomings of the prior art constructions.

Another and more specific object of the present invention aims at providing a new and improved construction of a dosing and mixing apparatus for fluid media in which a cleansing of the surfaces of the individual elements in mutual contact is performed simultaneously with the transfer procedure of the fluid media from one position into another.

Yet a further significant object of the present invention aims at providing a new and improved construction of a dosing and mixing apparatus of the character described which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds, the dosing and mixing apparatus of the present invention is manifested by the features that at least one channel is provided on a surface of one of the elements, such as the surface of the isolating element facing the delivery element and which is traversed by a cleansing fluid wetting the mutually facing surfaces of the individual elements in mutual contact in the transport path of the specimen quantity. This channel can be, however, also provided at the surface of the delivery element and which surface confronts the isolating element.

That is, either the delivery element or isolating element of the dosing and mixing apparatus for fluid media has a surface facing the other element, and a channel is provided in this surface. This channel is traversed by a cleansing fluid. This surface confronts a surface of the other element. The specimen quantity or measured dose of test specimen has a transport path and the cleansing fluid wets these confronting surfaces along the transport path.

In a dosing and mixing apparatus for fluid media having a two-component delivery element and an isolating element arranged therebetween to be rotatable about a shaft member and which elements are constructed as circular discs comprising transfer or through-flow passages suitably constructed and suitably peripherally distributed for delivering and mixing a voluminized specimen quantity or measured dose of test specimen with a voluminized thinning agent or measured dose of thinning agent, according to a further feature of the invention the intermediate isolating element is provided on both surfaces facing the components of the delivery elements with an inner and an outer annular channel, each communicating with circulation passages which are interconnected by a radially outwardly directed cross channel in the region of the transfer or through-flow passage provided in the rotating element.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 schematically shows a dosing and mixing apparatus in a first position in sectional view;

FIG. 2 shows the apparatus according to FIG. 1 in a second position;

FIG. 3 shows the apparatus according to the position illustrated in FIG. 2 in partial plan view;

FIG. 4 schematically shows a first alternate embodiment of a dosing and mixing apparatus in sectional FIG. 5 shows the apparatus according to FIG. 4 in a first position in plan view and on a reduced scale;

FIG. 6 shows the apparatus according to FIG. 4 in a second position in plan view and on a reduced scale;

DETAILED DESCRIPTION OF THE PREFERRED EMBODIMENTS

Figure 7:
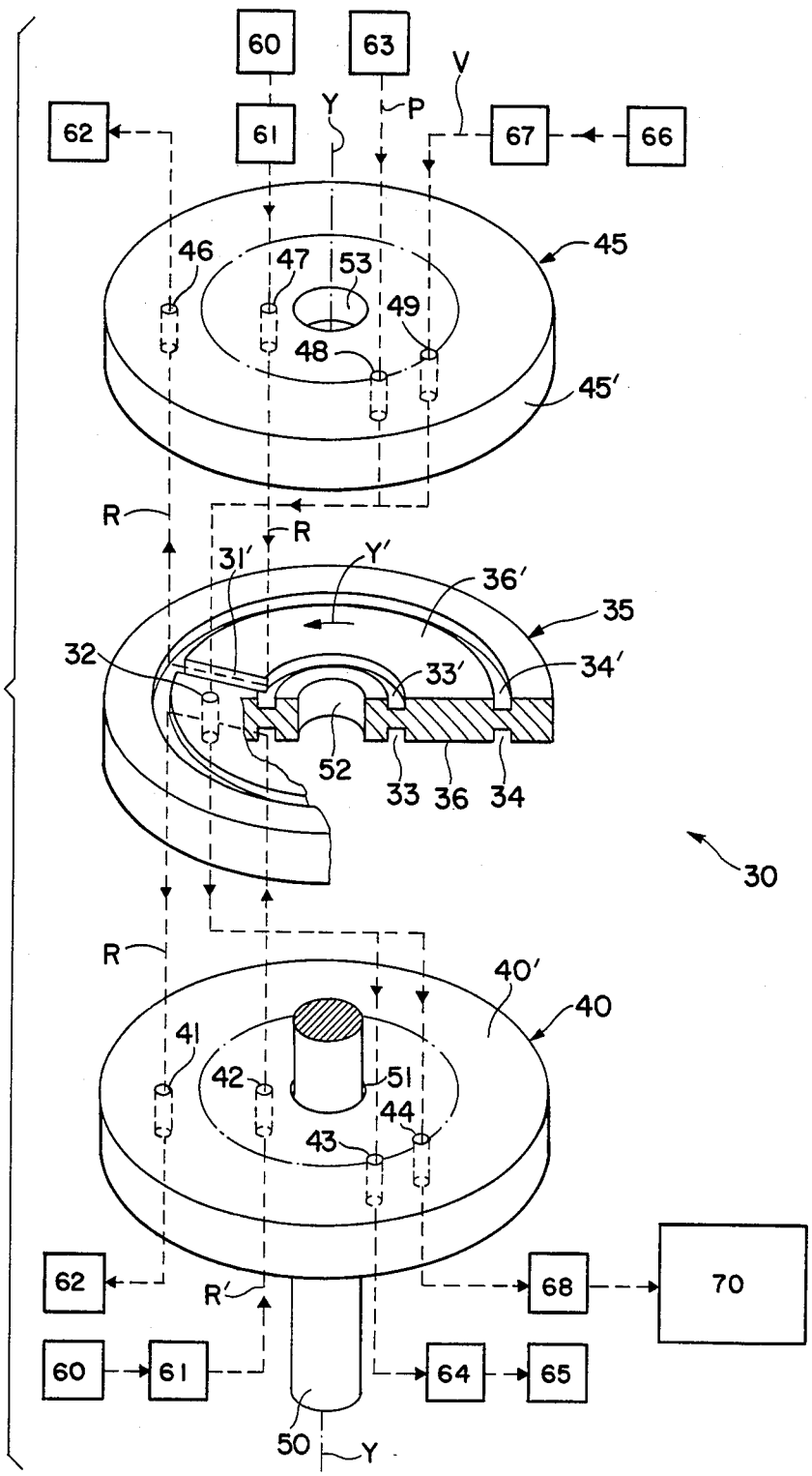
FIG. 7 schematically shows a second alternate embodiment of a dosing and mixing apparatus in isometric exploded view.

Describing now the drawings, it is to be understood that to simplify the showing thereof only enough of the structure of the dosing and mixing apparatus—also known as a sample segmenting and mixing apparatus—for fluid media has been illustrated therein as is needed to enable one skilled in the art to readily understand the underlying principles and concepts of this invention. Turning now specifically to FIG. 1 of the drawings, the apparatus illustrated therein by way of example and not limitation will be seen to comprise a dosing and mixing apparatus 10 which essentially comprises a stationary element or component 1 and a moveable element or component 5 linearly guided at its sides by any suitable and therefore not particularly shown guide means or the like in the direction of the arrow A. The upper stationary element 1, defining a delivery element, has at least four transfer passages or through-flow openings 2, 2', 3 and 3' arranged in mutual spaced relationship and having essentially parallel axes.

A circularly arcuate dosing or segmenting chamber 6 defining a dosing opening is arranged in the moveable element 5, defining an isolating or segmenting element, and opens into two mutually spaced transfer apertures or openings 6' and 6" in the transfer surface 5' facing and in contact with the delivery element 1. The spacing between the two transfer apertures 6' and 6" corresponds to the spacing of the transfer passages 2, 2" and 3, 3" arranged in the delivery element 1. The transfer apertures 6' and 6" coincide with the transfer passages 3 and 3" in the position illustrated in FIG. 2. Channels 4 and 7 are arranged in the upper transfer surface 5' of the isolating or segmenting element 5 facing the transfer surface 1' of the delivery element 1 in the region of each of the transfer apertures 6' and 6". The channel 4 is in communication with the lower surface 5" of the isolating element 5 via two bores or circulation passages 4' and 4" as can be seen in FIG. 2 and the channel 7 is in communication with the lower surface 5" of the isolating element 5 via two bores or circulation passages 7' and 7". A partially illustrated actuating arm 9 for effecting motion in the direction of the arrow A is arranged at one end of the isolating element 5.

FIG. 3 shows the dosing and mixing apparatus 10 in partial plan view in the position illustrated in FIG. 2. The two elements 1 and 5, the flow registering transfer passages and apertures 3, 6", and 3', 6' and the dosing or segmenting chamber 6 as well as the arcuate channels 4 and 7 oriented substantially transverse to the direction of motion A together with the bores or circulation passages 4', 4", 7' and 7" can be seen.

In FIG. 4 a first alternate embodiment of a dosing and mixing apparatus is designated with the reference character 20 and comprises a stationary element or component 25 and an element or component 21 pivotable along an arcuate path about a not particularly shown shaft member or pivot pin in the direction of the arrows B and B' as indicated in FIGS. 5 and 6. The upper pivotable element 21 has at least 23 and 23' arranged in mutual spaced relationship and corresponding to the pivoting motion. An annular channel 24 is arranged on the lower transfer surface 21' of the element 21, defining a delivery element, facing the element 25, defining the isolating or segmenting element, in the region of the transfer passages 22 and 22'. This annular channel 24 communicates with the upper surface 21" of the delivery element 21 via two bores or circulation passages 24' and 24". The transfer passages 23 and 23' are visible in FIG. 4 in shifted relationship.

The circulation passage 24' introduces a suitable cleansing fluid to the annular channel 24. The circulation passage 24" discharges the cleansing fluid from the annular channel 24. Thus a constant circulation of cleansing fluid is maintained in the annular channel 24 confronting the transfer surface 25'. Pivoting the component 21 in the direction of the arrows B and B' causes the annular channel 24 and therefore the cleansing fluid contained therein to sweep over and wet the transfer surface 25' both ahead of and behind the motion of the transfer passages 22 and 22' along the transfer surface 25'.

A circularly arcuate dosing chamber or opening 26 is arranged in the stationary isolating or segmenting element 25 and opens into two transfer apertures 26' and 26" arranged in mutually spaced relationship on the transfer surface 25' facing and in contact with the movable delivery element 21. The transfer passages 22, 22' and 23, 23' are mutually arranged such that they register or coincide with the transfer apertures 26' and 26" of the dosing chamber 26 in each position following the pivoting motion in the direction of the arrow B, respectively B', as shown in FIGS. 5 and 6.

FIG. 7 shows a preferred exemplary embodiment of a dosing and mixing apparatus 30 in isometric exploded view which substantially comprises a first stationary element 40, a moveable element 35 as well as a second stationary element 45. The elements 35, 40 and 45 will be individually described in the following.

The upper stationary element 45, defining one part of a two part delivery element, is constructed as a circular disc and is provided with a plurality of through-flow passages or openings comprising circulation passages 46 and 47 as well as transfer passages 48 and 49 and also with a central bore 53. The lower stationary element 40, defining the other part of the two part delivery element, is also constructed as a circular disc with a plurality of through-flow passages or openings defining circulation passages 41 and 42 and transfer passages 43 and 44 as well as with a central bore 51.

The intermediate moveable element 35, defining an isolating or segmenting element, is constructed, for instance, as a circular disc and, in the assembled state, is arranged in contact with and between the upper and lower elements 45 and 40. An outer annular channel 34, 34' as well as an inner annular channel 33, 33' is provided on each of the lower and upper surfaces 36 and 36', respectively, of the isolating element 35 facing the elements 40 and 45. Both channels 33' and 34' are interconnected by a cross channel 31' and the channels 33 and 34 are also interconnected by an analogous cross channel 31 not particularly shown or designated in FIG. 7 but visible in FIG. 8. A dosing or segmenting chamber 32 is provided in the isolating or segmenting element 35 immediately in the region of the cross channel 31'. The isolating element 35 is rotatable in the direction of the arrow Y' by any suitable, and therefore not particularly shown drive means and is penetrated by a central bore 52.

The charging and flow system is also schematically represented in relation to the previously described dosing and mixing apparatus 30 in FIG. 7. This charging and flow system substantially comprises first and second supply reservoirs or containers 60 and 60', first and second pumps 61 and 61' associated with the supply reservoirs or containers 60 and 60', first and second collection reservoirs or containers 62 and 62', a specimen container 63, a further pump 64, a collection container or reservoir 65, a supply container or reservoir 66, a pump 67 associated with the supply container or reservoir 66, a product container 68 as well as an analysis device 70 associated with the product container 68.

Figure 8:
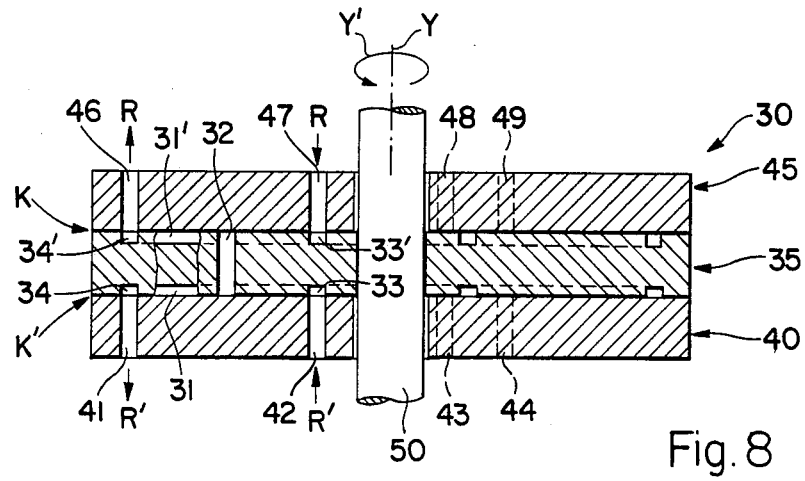
FIG. 8 shows the apparatus according to FIG. 7 in a first position in sectional view.

The dosing and mixing apparatus 30 according to FIG. 7 is shown in a first position in FIG. 8. Both stationary elements 40 and 45 with the suitably mutually correspondingly arranged through-flow passages 41, 42, 43 and 44 as well as 46, 47, 48 and 49 are visible. The intermediate isolating element 35 provided with the dosing or segmenting chamber 32 is arranged between the two elements 40 and 45 defining the two-part delivery element and is rotatable by suitable not particularly shown drive means about the axis of symmetry Y of the shaft member 50 in the direction of the arrow Y' in relation to the two elements 40 and 45.

Figure 9:
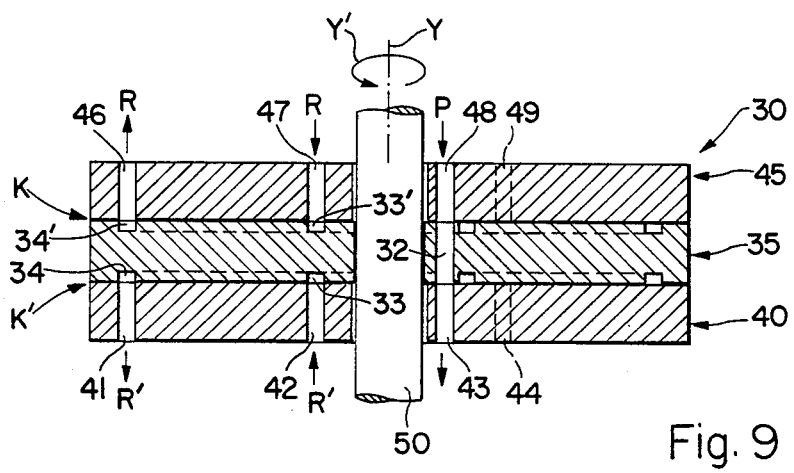
FIG. 9 shows the apparatus according to FIG. 7 in a second position in sectional view.

The dosing and mixing apparatus 30 is shown in a second position in sectional view in FIG. 9. The section is taken through the two transfer passages 43 and 48 of the elements 40 and 45 and the intermediate element 35 has been rotated in the direction of the arrow Y' such that the transfer passages 48 and 43 and the dosing chamber 32 register or coincide with one another.

Figure 10:
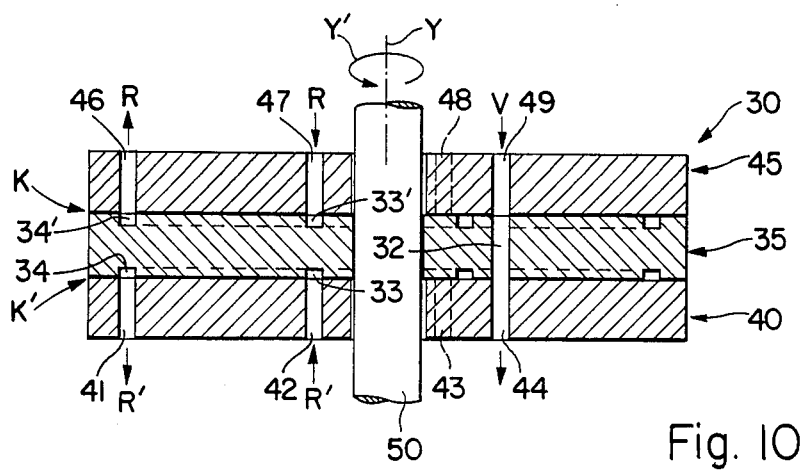
FIG. 10 shows the apparatus according to FIG. 7 in a third position in sectional view.

The dosing and mixing apparatus 30 is shown in a third position in sectional view in FIG. 10. The section is taken through the two transfer passages 44 and 49 of the elements 40 and 45 and the intermediate element 35 has been further rotated in the direction of the arrow Y' such that now the transfer passages 49 and 44 and the dosing chamber 32 register or coincide with one another In FIGS. 8, 9 and 10 the circulation passages 46 and 47 arranged in the upper element 45, the circulation passages 41 and 42 arranged in the lower element 40 as well as the annular channels 33, 33', 34 and 34' arranged in the intermediate element 35 and correspondingly associated with the circulation passages 41, 42, 46 and 47 of the elements 40 and 45 are visible. The circulation passages 46 and 47 communicate with the annular channels 34' and 33' and the circulation passages 41 and 42 communicate with the annular channels 34 and 33. The annular channels 33' and 34' are operatively interconnected by the cross channel 31' shown in partial view in FIG. 8 and the annular channels 33 and 34 are operatively interconnected by the cross channel 31 also shown in partial view in FIG. 8.

The previously described dosing and mixing apparatuses 10, 20 and 30 serve for the dosing or segmenting of fluids which is known as such, and especially for accommodating and isolating or segmenting a voluminized blood specimen or measured dose of blood specimen in the microlitre range, as well as for the transport and the mixing of this blood specimen with a voluminized quantity of or measured dose of a suitable thinning fluid or agent i.e. diluent.

In the dosing and mixing apparatus 10, the specimen quantity brought in known manner into the dosing chamber 6 is transported from the position shown in FIG. 1 into the position shown in FIG. 2 by a substantially linear transport motion in the direction of the arrow A. In this position the specimen quantity is mixed with the thinning fluid or diluent and conducted to a not particularly shown analysis device, such as the analysis device 70 shown in FIG. 7. In the transport procedure, the channels 4 and 7 are traversed by a suitable cleansing fluid and the surfaces 1' and 5' of the elements 1 and 5 wetted by the specimen quantity are thereby cleansed.

In the dosing and mixing apparatus 20, the specimen quantity brought into the dosing chamber 26 is transported into the appropriate position by a pivoting motion in the direction of the arrows B and B'. As the specimen is transferred from the position in which it is introduced or filled into the dosing chamber 26 by the transfer passages 22 and 22' to the position in which it is discharged by the transfer passages 23 and 23', the cleansing fluid contained in the annular channel 24 wets the confronting transfer surface 25' and thus provides a comprehensive cleansing action, flushing away any possible contaminants, carry-overs or deposits upon the confronting transfer surface 25' ahead of the transfer passage 22 containing specimen material in excess of the dose or measured quantity contained in the dosing chamber 26 and also flushing away any possible carry-overs or deposits left behind by the transfer passage 22' also containing specimen material in excess of the dose or measured quantity in the dosing chamber 26. Since the annular channel 24 openly confronts the dosing chamber 26, the cleansing fluid must be chosen such taht it is immiscible with the fluid of the specimen, for instance haemophobic. Due to the isolation of the dosing chamber 26 during the transfer operation, there is no resultant pressure tending to introduce the cleansing fluid into the dosing chamber 26 and it is therefore only necessary to ensure that the cleansing fluid and the speciment material are mutually repellant. In this manner, on the one hand, the surfaces 21' and 25' of the elements 21 and 25 wetted by the specimen quantity are cleansed and, on the other hand, the transfer passages 22, 22', 23 and 23' opening into the wetted surfaces 21' and 25' are surrounded by the annular channel 24 and a leakage of the individual media is thereby inhibited.

In the dosing and mixing apparatus 30, the intermediate element 35 is rotated out of the position shown in FIG. 8 and into the position shown in FIG. 9 according to the direction of the arrow Y'. The dosing chamber 32 for accommodating the specimen quantity coincides or registers with the transfer passages 43 and 48 of the elements 40 and 45.

In a further rotary motion in the direction of the arrow Y' the column of specimen quantity brought into the dosing chamber 32 is now isolated or segmented and transported into the position shown in FIG. 10 in which position the dosing chamber 32 now registers or coincides with the transfer passages 44 and 49 for accommodating the thinning fluid or diluent. The medium (product) formed from the specimen quantity and the thinning fluid or diluent is subsequently conducted to the analysis device 70.

In the dosing and mixing procedure of the apparatus 30, the wetted surfaces 36, 40' and 36', 45' of the individual elements 35, 40 and 45 are cleansed by the cross channels 31 and 31' extending radially outward and interconnecting the annular channels 33, 34 and 33', 34', while these annular channels 33, 34 and 33', 34' communicating with the circulation passages 41, 42 and 46, 47 are constantly traversed by the cleansing fluid or agent.

In FIG. 7 the flow directions of the individual media are illustrated in broken line and with arrows and are also shown in FIGS. 8, 9 and 10 with arrows only. The cleansing fluid is designated with the reference characters R and R' while the specimen quantity is designated with the reference character P and the thinning fluid or diluent is designated with the reference character V.

In the exemplary embodiments of the dosing and mixing apparatuses 20 and 30 according to FIGS. 4 through 10, the annular channels 24, respectively the inner and outer annular channels 33, 33', 34 and 34', in addition to their cleansing action, also inhibit a leakage of the thinning fluid or diluent (for instance sodium chloride solution), whereby any crystallization detrimental to operation at the contact positions designated with the reference character K in FIGS. 8, 9 and 10 of the individual elements is avoided.

Figure 11:
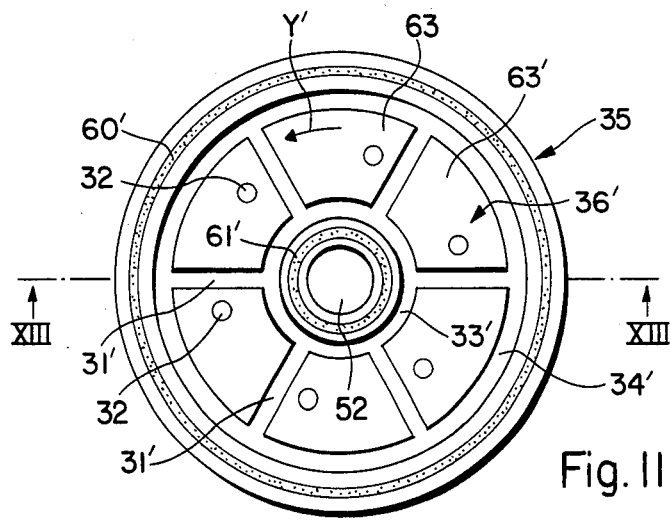
FIG. 11 illustrates a modification of the embodiment depicted in FIGS. 7 to 10, specifically the upper surface of the movable isolating or segmenting element.
Figure 12:
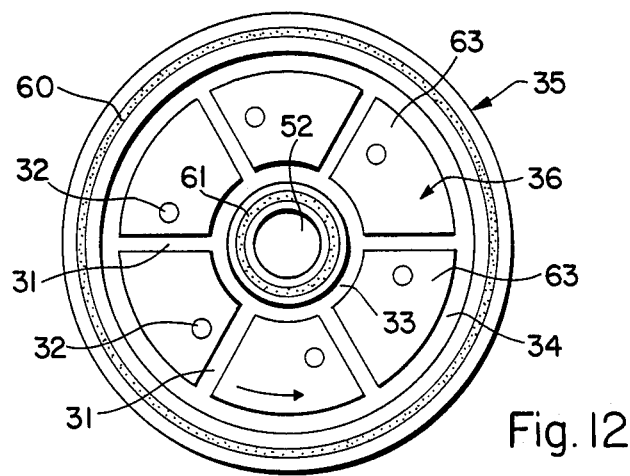
FIG. 12 illustrates the lower surface of the movable isolating or segmenting element depicted in FIG. 11.

In a further exemplary embodiment of the dosing and mixing apparatus illustrated in FIGS. 11 and 12, the surfaces 36 and 36' of the intermediate element 35 facing the elements 40 and 45 can be subdivided into several segmental surface elements. Each surface element can be provided with a corresponding dosing chamber 32 and can be further subdivided by a cross channel 31 interconnecting the annular channels 33 and 34, respectively 33' and 34'.

Figure 13:
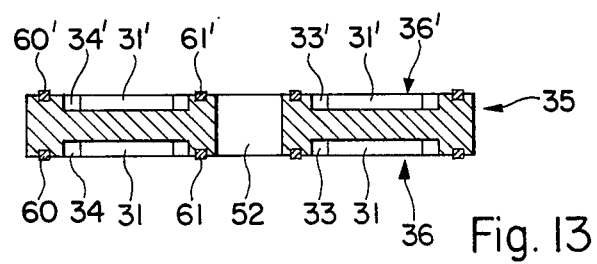
FIG. 13 illustrates in sectional view a further modification of the movable isolating or segmenting element depicted in FIG. 11, the section being taken along the lines XIII—XIII thereof, and illustrating such modified movable isolating or segmenting element provided with gaskets at the upper and lower surfaces thereof.

In yet further exemplary embodiment of the dosing mixing apparatus 30 illustrated in FIG. 13, the intermediate element 35 is provided with suitably arranged gaskets 60 and 60' on the surfaces 36 and 36' facing the two elements 40 and 45. These gaskets 60 and 60' are seated in appropriate grooves and should have an optimum surface smoothness. They are arranged in the region between the outer channels 34 and 34' and the circumferential outer edge of the apparatus as well as between the inner channels 33 and 33' and the central bore 52 of the element 35.

It will be understood that the moveable elements 5 and 35 have a medium-isolating or segmenting function and the stationary elements 1, 40 and 45 have a medium-delivering function.

While there are shown and described present preferred embodiments of the invention, it is to be distinctly understood that the invention is not limited thereto, but may be otherwise variously embodied and practiced within the scope of the following claims. Accordingly,

What we claim is:

1. A dosing and mixing apparatus for fluid media, comprising:
    at least one isolating element;
    at least one delivery element;
    said at least one isolating element and said at least one delivery element each including through-flow openings therein;
    said through-flow openings serving for accommodating and isolating at least one measured dose of test specimen as well as for delivering said at least one measured dose of test specimen to and mixing said at least one measured dose of test specimen with a diluent;
    a first surface provided on one element of either said at least one isolating element or said at least one delivery element and facing another element of either said at least one isolating element or said at least one delivery element;
    with the proviso that when said one element constitutes an isolating element said other element constitutes a delivery element and when said one element constitutes a delivery element said other element constitutes an isolating element;
    at least one channel provided in said first surface of said one element;
    circulation passages provided in said one element and in flow communication with said at least one channel for permitting flow of a cleansing fluid therethrough independently of positional relationships between said at least one isolating element and said at least one delivery element;
    a second surface provided on said other element and facing said first surface;
    said first and second surfaces being in mutual contact; and
    said at least one channel constituting means for wetting said first and second surface with said cleaning fluid during such time as the at least one isolated measured dose of test specimen is moved along a predetermined transport path.

2. The dosing and mixing apparatus as defined in claim 1, wherein:
    said through-flow openings of said at least one isolating element define respective dosing chambers having transfer apertures at outer ends thereof;
    said at least one channel being aligned with pairs of said transfer apertures and;
    said at lest one channel being substantially arcuate.

3. The dosing and mixing apparatus as defined in claim 1, wherein:
    said through-flow openings of said at least one isolating element define respective dosing chambers having transfer apertures at outer ends thereof;
    said at least one channel being aligned with pairs of said transfer aperatures and;
    said at least one channel being annular.

4. The dosing and mixing apparatus as defined in claim 1, wherein:
    said at least one isolating element is moveable relative to said at least one delivery element.

5. A dosing and mixing apparatus for fluid media, comprising:
    at least one isolating element;
    at least one delivery element;
    said at least one isolating element and said at least one delivery element each including through-flow openings therein;

said through-flow openings serving for accommodating and isolating at least one measured dose of test specimen as well as for delivering the at least one measured dose of test specimen to and mixing the at least one measured dose of test specimen with a diluent;

one of said elements being movable relative to another one of said elements;

with the proviso that when said one element constitutes an isolating element then said other element constitutes a delivery element and said element which is movable relative to the other element is said isolating element;

and with the further proviso that when said one element constitutes a delivery element then said other element constitutes an isolating element and said element which is movable relative to the other element is said delivery element;

a first surface provided on said one element;

at least one channel provided in said first surface of said one element;

circulation passages provided in said one element and in flow communication with said at least one channel for permitting flow of a cleansing fluid therethrough independently of movement relationships between adjacent ones of said at least one isolating element and said at least one delivery element;

a second surface provided on the other and facing said first surface;

said first and second surfaces being in mutual contact with one another; and said at least one channel constituting means for wetting said first and second surfaces with a cleansing fluid when the one isolated measured dose of test specimen is moved along a predetermined transport path.

6. The dosing and mixing apparatus as defined in claim 5, wherein:

said one element which is moveable relative to the other element is substantantially linearly moveable.

7. The dosing and mixing apparatus as defined in claim 5, wherein:

said one element which is moveable relative to the other element is moveable along a substantially arcuate path of travel.

8. The dosing and mixing apparatus as defined in claim 5, wherein:

said first and second surfaces define transfer surfaces between which the at least one isolated measured dose of test specimen is transferred from one of said elements to the other of said elements.

9. A dosing and mixing apparatus for fluid media, comprising;

a shaft member;

a delivery element having two parts;

an isolating element rotatable about said shaft member and located between said two parts of said delivery element;

said delivery element and said isolating element comprise disc-shaped elements and including through-flow openings therein;

said through-flow openings serving for delivering a measured dose of test specimen to and mixing said measured dose of test specimen with a diluent;

said isolating element having two surfaces each facing a respective one of said two parts of said delivery element;

said isolating element being provided with a first annular channel and a second annular channel formed in each of said two surfaces;

said second annular channel being spaced radially outward of said first annular channel;

said first annular channel and said second annular channel each communicating with said through-flow openings of said delivery element;

a through-flow opening of said isolating element defining at least one dosing chamber; and radially aligned cross channels formed in the respective surfaces of the isolating element and interconnecting said first annular channel and said second annular channel in the region of said dosing chamber for circulating a cleaning fluid across a path of travel of said through-flow opening of said isolating element.

10. The dosing and mixing apparatus as defined in claim 9, further including:

a plurality of said dosing chambers;

said radially outwardly directed cross channels being distributed about said two surfaces of said isolating element;

said radially outwardly directed cross channels dividing said two surfaces of said isolating element into individual segmental surface portions; and each said cross channel being associated with one of said plurality of dosing chambers.

11. The dosing and mixing apparatus as defined in claim 9, further including:

two outer gaskets and two inner gaskets arranged upon said two surfaces of said isolating element; and said gaskets sealing said isolating element in relation to said two parts of said delivery element.

12. A dosing and mixing apparatus for fluid media, comprising:

at least one isolating element;

at least one delivery element;

said at least one isolating element having a first surface;

said at leat one isolating element being provided with a dosing chamber having at least one first opening at said first surface;

said at least one delivery element having a second surface;

said at least one delivery element being provided with at least two transfer passages each having at least one second opening at said second surface;

said at least one isolating element and said at least one delivery element being mutually arranged such that said first surface and said second surface are in mutually translatable contact for selectively aligning predetermined ones of said at least one second openings with said at least one first opening;

said at least one isolating element being provided with a cleansing medium supply passage and a cleansing medium discharge passage interconnected to at least one cleansing channel formed in said first surface; and said at least one cleansing channel extending across a path of translation of said at least one second openings relative to said at least one first opening and presenting a channel side open to said second surface for wetting said second surface with a cleansing medium circulated through said cleansing medium supply passage, said cleansing channel and said cleansing medium discharge passage.

* * * * *

UNITED STATES PATENT AND TRADEMARK OFFICE
CERTIFICATE OF CORRECTION

PATENT NO. : 4,726,932

DATED : February 23, 1988

INVENTOR(S) : Markus FEIER et al

It is certified that error appears in the above-identified patent and that said Letters Patent is hereby corrected as shown below:

Column 3, line 2, at the end of the line, after "sectional" please add --view;--

Column 4, line 20, after "least" please insert --four transfer or through-flow passages or openings 22, 22',--

Column 6, line 51, please delete "taht" and insert --that--

Column 7, line 47, before "yet" please insert --a-- and after "dosing" please insert --and--

Column 8, line 38, at the end of the line, please delete "cleaning" and insert --cleansing--

Column 8, line 48, please delete "and;" and after "apertures" insert --;and--

Column 8, line 49, please delete "lest" and insert --least--

Column 8, line 56, please delete "aperatures and;" and insert --apertures; and--

Column 9, line 29, after "other" please insert --element--

Column 10, line 15, please delete "cleaning" and insert --cleansing--

Column 10, line 41, please delete "leat" and insert --least--

UNITED STATES PATENT AND TRADEMARK OFFICE
CERTIFICATE OF CORRECTION

PATENT NO. : 4,726,932

DATED : February 23, 1988

INVENTOR(S) : Markus FEIER et al

It is certified that error appears in the above-identified patent and that said Letters Patent is hereby corrected as shown below:

Column 10, line 58, please delete "to" and insert --by--

Signed and Sealed this

Twenty-third Day of August, 1988

Attest:

DONALD J. QUIGG

Attesting Officer

Commissioner of Patents and Trademarks